United States Patent
Watson et al.

(10) Patent No.: US 6,685,319 B2
(45) Date of Patent: Feb. 3, 2004

(54) ENHANCED WAVEFRONT ABLATION SYSTEM

(75) Inventors: Jason Watson, San Jose, CA (US); John K. Shimmick, Belmont, CA (US)

(73) Assignee: Visx, Incorporated, Santa Clara, CA (US)

( * ) Notice: Subject to any disclaimer, the term of this patent is extended or adjusted under 35 U.S.C. 154(b) by 73 days.

(21) Appl. No.: 09/960,163

(22) Filed: Sep. 20, 2001

(65) Prior Publication Data

US 2002/0097375 A1 Jul. 25, 2002

Related U.S. Application Data

(60) Provisional application No. 60/234,452, filed on Sep. 21, 2000.

(51) Int. Cl.[7] .................................................. A61B 3/00
(52) U.S. Cl. ...................................................... 351/219
(58) Field of Search ................................ 351/205, 212, 351/216, 219, 221, 222, 227, 230, 233, 239, 246, 247; 600/558; 606/5, 107; 607/89; 128/898

(56) References Cited

U.S. PATENT DOCUMENTS

| | | |
|---|---|---|
| 4,838,679 A | 6/1989 | Bille |
| 5,463,200 A | 10/1995 | James et al. |
| 5,502,520 A | 3/1996 | Cibis et al. |
| 5,557,352 A * | 9/1996 | Nordquist .................... 351/246 |
| 5,683,379 A | 11/1997 | Hohla |
| 5,713,892 A | 2/1998 | Shimmick |
| 5,777,719 A * | 7/1998 | Williams et al. ............. 351/212 |
| 5,941,874 A * | 8/1999 | Hohla ............................. 606/5 |
| 5,949,521 A | 9/1999 | Williams et al. |
| 6,050,687 A | 4/2000 | Bille et al. |
| 6,086,204 A | 7/2000 | Magnante |
| 6,095,651 A | 8/2000 | Williams et al. |
| 6,155,684 A | 12/2000 | Bille et al. |
| 6,199,986 B1 | 3/2001 | Williams et al. |

(List continued on next page.)

OTHER PUBLICATIONS

Asclepion Meditec Annual Report 1999/2000, Asclepion–Meditec AG, Pruessingtrasse 41, 07745 Jena, Germany, Phone: (+49) 364165–3223, pp. 1, 8–13 and 26–27.

20/10 Perfect Vision™ Press Release dated Oct. 11, 2000 entitled "20/10 Perfect Vision™ Announces First Wavefront–Driven Custom Ablations Performed", 2 pages total.

20/10 Perfect Vision™ Press Release dated Jan. 12, 2001 entitled "20/10 Perfect Vision™ Reports Excellent Wavefront–Driven Custom Ablation Results", 2 pages total.

20/10 Perfect Vision™—Technology—Improving Vision web page http://www.2010pv.com/tech_b_1.htm ©2000/2001, 1 page total.

George, P., "New Wavefront Devices could mean Superior Vision for LASIK Patients" web article dated Feb. 2002 from http://www.ienhance.com/article/detail.asp?ArtID=173, 3 pages total.

Opto Electronics S.A. Medical Division, web article dated Feb. 27, 2001 from http://www.opto.com/br/english/medicaldiv/products/Wavefront–2010PV.htm, 5 pages total.

Primary Examiner—Dennis Ruhl
Assistant Examiner—John R Sanders
(74) Attorney, Agent, or Firm—Townsend & Townsend & Crew LLP; Mark D. Barrish, Esq.

(57) ABSTRACT

Systems and methods verify and/or correct optical errors of an eye. A plan is generated for a corrective procedure of the eye from a measured optical error, and a verification lens is formed based on the measured optical error to verify the procedure plan. Alignment of an aperture (with a size selected to correspond to the size of the pupil) with the eye while measuring optical properties of the eye through the verification lens improves verification accuracy, as does mounting of the verification lens and aperture to the patient with a trial frame.

11 Claims, 9 Drawing Sheets

FIG. 1

U.S. PATENT DOCUMENTS

| | | |
|---|---|---|
| 6,220,707 B1 | 4/2001 | Bille |
| 6,296,358 B1 | 10/2001 | Cornsweet et al. |
| 6,299,306 B1 | 10/2001 | Braithwaite et al. |
| 6,299,311 B1 | 10/2001 | Williams et al. |
| 6,338,559 B1 | 1/2002 | Williams et al. |
| 6,419,671 B1 * | 7/2002 | Lemberg .................. 606/5 |

* cited by examiner

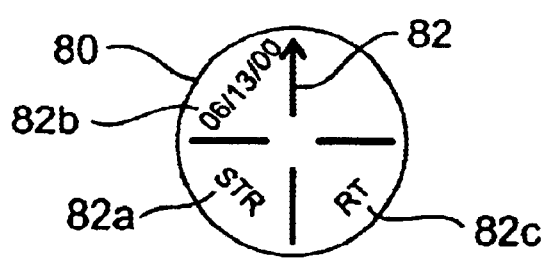 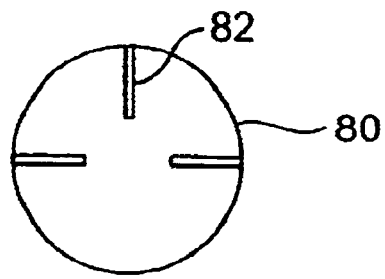
FIG. 4A              FIG. 4B
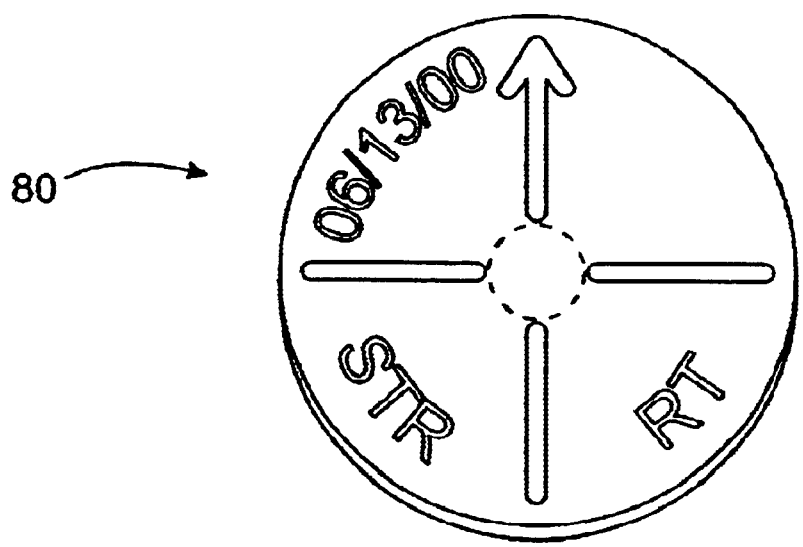
FIG. 4C

ENHANCED WAVEFRONT ABLATION SYSTEM

CROSS-REFERENCES TO RELATED APPLICATIONS

The present application is a regular patent application of and claims the benefit of priority from U.S. Provisional Patent Application No. 60/234,452 filed Sep. 21, 2000, the full disclosure of which is incorporated herein by reference.

BACKGROUND OF THE INVENTION

Field of the Invention

The present invention is generally related to vision correction systems. In one embodiment, the invention provides systems and methods for verifying a refractive surgical procedure, ideally by ablating a customized corrective lens before imposing a corresponding refractive correction in the corneal tissues.

Known laser eye procedures generally employ an ultraviolet or infrared laser to remove a microscopic layer of stromal tissue from the cornea of the eye to alter the refractive characteristics of the eye. The laser removes a selected shape of the corneal tissue, often to correct refractive errors of the eye. Ultraviolet laser ablation results in photodecomposition of the corneal tissue, but generally does not cause significant thermal damage to adjacent and underlying tissues of the eye. The irradiated molecules are broken into smaller volatile fragments photochemically, directly breaking the intermolecular bonds.

Laser ablation procedures can remove the targeted stroma of the cornea to change the cornea's contour for varying purposes, such as for correcting myopia, hyperopia, astigmatism, and the like. Control over the distribution of ablation energy across the cornea may be provided by a variety of systems and methods, including the use of ablatable masks, fixed and moveable apertures, controlled scanning systems, eye movement tracking mechanisms, and the like. In known systems, the laser beam often comprises a series of discrete pulses of laser light energy, with the total shape and amount of tissue removed being determined by the shape, size, location, and/or number of a pattern of laser energy pulses impinging on the cornea. A variety of algorithms may be used to calculate the pattern of laser pulses used to reshape the cornea so as to correct a refractive error of the eye. Known systems make use of a variety of forms of lasers and/or laser energy to effect the correction, including infrared lasers, ultraviolet lasers, femtosecond lasers, wavelength multiplied solid-state lasers, and the like. Alternative vision correction techniques make use of radial incisions in the cornea, intraocular lenses, removable corneal support structures, thermal shaping, and the like.

Known corneal correction treatment methods have generally been successful in correcting standard vision errors, such as myopia, hyperopia, astigmatism, and the like. However, as with all successes, still further improvements would be desirable. Toward that end, wavefront measurement systems are now available to measure the refractive characteristics of a particular patient's eye. By customizing an ablation pattern based on wavefront measurements, it may be possible to correct minor refractive errors so as to reliably and repeatably provide visual accuities greater than 20/20. Alternatively, it may be desirable to correct aberrations of the eye that reduce visual acuity to less than 20/20. Unfortunately, these measurement systems are not immune from measurement error. Similarly, the calculation of the ablation profile, the transfer of information from the measurement system to the ablation system, and the operation of the ablation system all provide opportunities for the introduction of errors, so that the actual visual accuities provided by real-world wavefront-based correction systems may not be as good as might be theoretically possible.

In light of the above, it would be desirable to provide improved vision correction systems and methods.

SUMMARY OF THE INVENTION

In a first aspect, the present invention provides a method comprising measuring an actual optical error of an eye. A plan is generated for a corrective procedure of the eye from the measured optical error. A verification lens is formed based on the measured optical error to verify the procedure plan.

Optionally, irregular optical error of the eye can be measured so that the verification lens compensates for the irregular error. In many embodiments, a wavefront of light passing through the optical components of the eye will be measured with a wavefront sensor to measure the refractive error of the eye. The verification lens can be generated by ablating a lens material according to an ablation pattern.

The ablation pattern for the verification lens can be calculated from the measured optical error of the eye, and from characteristics of the lens material, such as a refractive index of the lens material, a rate of ablation of the lens material, and/or a shape of ablation of the lens material (for example, the propensity of the lens material to differ in ablation depth across a uniform ablation energy beam, such as any "central island" properties of the lens material). A corneal tissue of the eye may be ablated according to an ablation pattern, and the ablation pattern may similarly be calculated based on the measured optical error of the eye and on the corneal tissue characteristics, such as a refractive index of the corneal tissue, a rate of ablation of the corneal tissue, and/or a shape of ablation of the corneal tissue.

In another aspect, the invention also provides a method comprising measuring an actual optical error of an eye of a patient with a wavefront sensor, and also measuring a pupil size of the eye. An ablation pattern is generated from the measured optical error, and an ablation pattern is also generated for lens material, the lens material pattern corresponding to the ablation pattern for the eye. The lens material is positioned relative to an ablation system by aligning indicia of the lens material with a reticule of the ablation system. A verification lens is ablated in the aligned lens material with the ablation system according to the lens pattern. An aperture is aligned with the verification lens, with the aperture size selected in response to the pupil size of the eye. The verification lens and the aperture are mounted to the patient so that the eye is aligned with the verification lens, and an eye chart is viewed with the eye through the verification lens and the aperture to determining whether a corrected visual acuity of the eye is within an acceptable range so as to verify the ablation pattern of the eye.

In other aspects, the invention also provides related systems for verifying and/or correcting optical errors of an eye.

BRIEF DESCRIPTION OF THE DRAWINGS

FIGS. 4A-C illustrate a verification lens material.

DESCRIPTION OF THE SPECIFIC EMBODIMENTS

The present invention is particularly useful for enhancing the accuracy and efficacy of laser eye surgical procedures such as photorefractive keratectomy (PRK), phototherapeutic keratectomy (PTK), laser in situ keratomileusis (LASIK), and the like. Preferably, the present invention can provide verification of the improvement of the optical system in the eye and provide feedback to surgeons before the vision correction procedures. Hence, although the system is described in the context of a laser eye surgery system, it should be understood the system may be adapted for use in alternative eye treatment procedures and systems such as for use in radial keratotomy, intraocular lenses, corneal ring implants, and the like. All references referred to in this application are hereby incorporated herein by reference.

The system of the present invention can be easily adapted for use with existing laser systems. By providing verification of actual improvements of the optical system in the eye, the present invention also allows the surgeon to evaluate the procedure plan, and whether additional measurements or an alternative plan should be prepared. Thus, the feedback provided by the present invention may facilitate sculpting of the cornea so that the eye exceeds the normal 20/20 threshold of desired vision.

Figure 1:
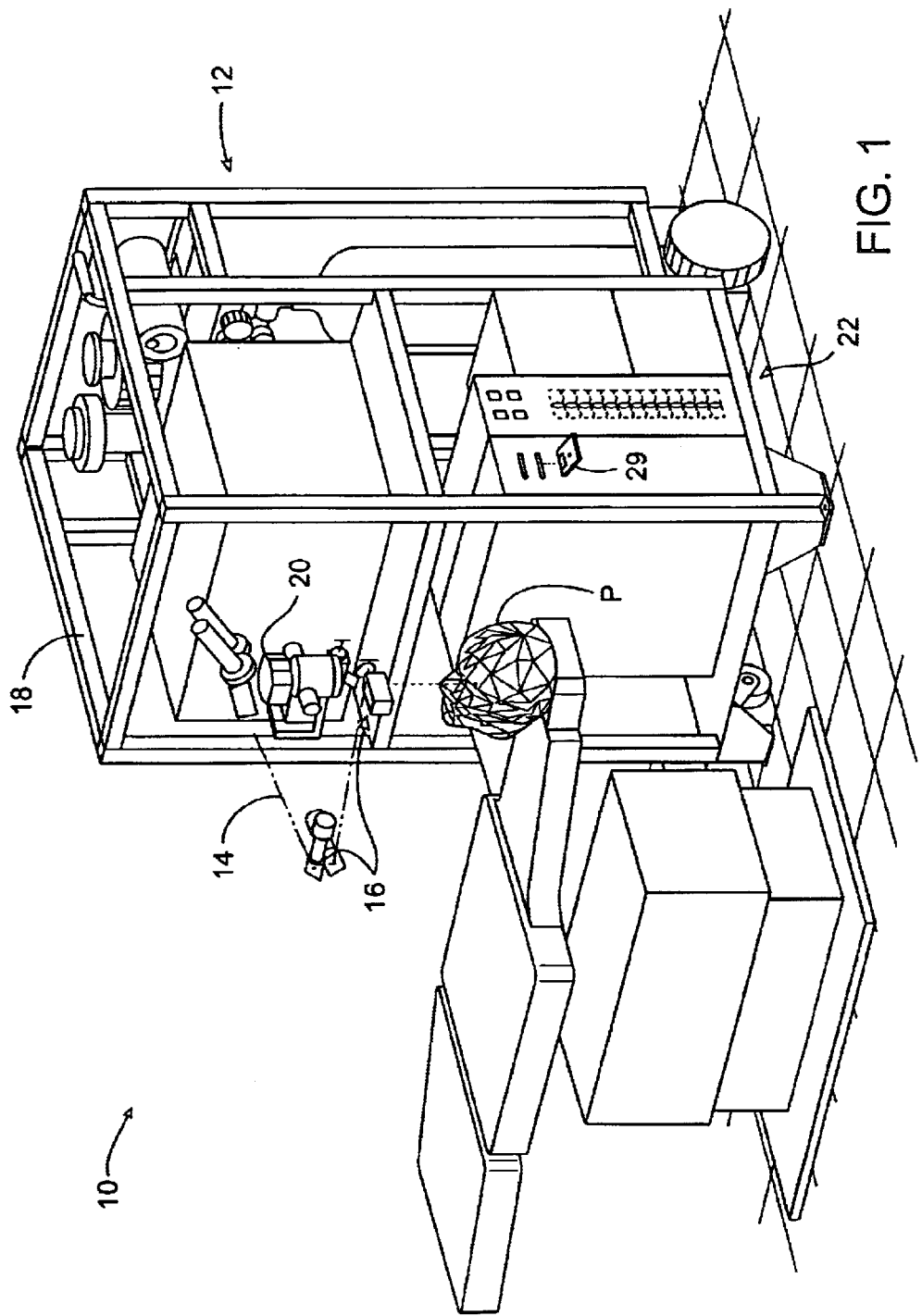
FIG. 1 is an overview of a laser ablation system.

Referring now to FIG. 1, a laser eye surgery system 10 of the present invention includes a laser 12 that produces a laser beam 14. Laser 12 is optically coupled to laser delivery optics 16, which directs laser beam 14 to an eye of patient P. A delivery optics support structure (not shown here for clarity) extends from a frame 18 supporting laser 12. A microscope 20 is mounted on the delivery optics support structure, the microscope often being used to image a cornea of eye E.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser 12 and delivery optics 16 will generally direct laser beam 14 to the eye of patient P under the direction of a computer 22. Computer 22 will generally selectively adjust laser beam 14 to expose portions of the cornea to the pulses of laser energy so as to effect a predetermined sculpting of the cornea and alter the refractive characteristics of the eye. In many embodiments, both laser 14 and the laser delivery optical system 16 will be under computer control of processor 22 to effect the desired laser sculpting process, with the processor ideally altering the ablation procedure in response to inputs from the optical feedback system described hereinbelow. The feedback will preferably be input into processor 22 from an automated image analysis system, or may be manually input into the processor by a system operator using an input device in response to a visual inspection of analysis images provided by the optical feedback system. Processor 22 will often continue and/or terminate a sculpting treatment in response to the feedback, and may optionally also modify the planned sculpting based at least in part on the feedback Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. No. 5,683,379, and as also described in co-pending U.S. patent application Ser. No. 08/968,380, filed Nov. 12, 1997; and Ser. No. 09/274,999 filed Mar. 22, 1999, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913 (the full disclosure of which is incorporated herein by reference) and as demonstrated by other scanning laser systems such as the LSX laser by LaserSight, LadarVision by Alcon/Autonomous, and the 217C by Technolas; using masks in the optical path of laser beam 14 which ablate to vary the profile of the beam incident on the cornea, as described in U.S. patent application Ser. No. 08/468,898, filed Jun. 6, 1995 (the full disclosure of which is incorporated herein by reference); hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the disclosure of which is incorporated herein by reference. An ablation effluent evacuator/filter, and other ancillary components of the laser surgery system which are not necessary to an understanding of the invention, need not be described in detail for an understanding of the present invention.

As mentioned above, laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying steps or programming instructions for any of the methods of the present invention. Tangible storage media 29 may take the form of a floppy disk, an optical disk, a data tape, a nonvolatile memory, or the like, and the processor 22 will include the memory boards and other standard components of modern computer systems for storing and executing this code.

Figure 2:
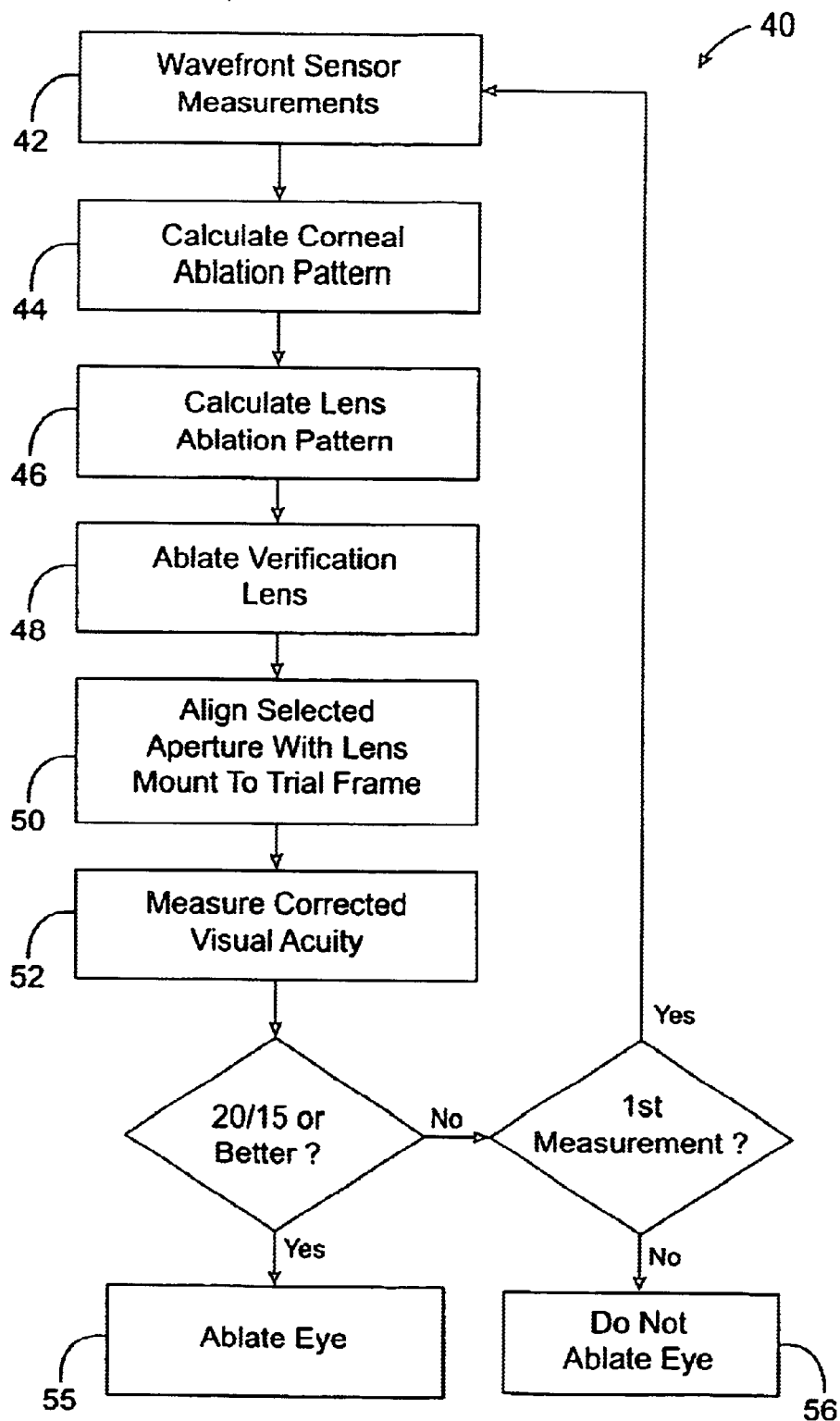
FIG. 2 is a flow chart schematically illustrating an exemplary ablation verification and optical error correction method.

Referring now to FIG. 2, an exemplary verification/refractive correction method 40 can verify that an intended ablation is appropriate for a particular eye. Measurements of the eye are taken, ideally to determine both standard refractive errors (such as myopia, hyperopia, and/or astigmatism) and irregular refractive errors (optionally including any other optical errors of the optical system of the eye). In the exemplary method, the optical errors of the eye are measured with a wavefront sensor system 42, such as the WaveScan system available commercially from 2010 Perfect Vision, the system described in U.S. Pat. No. 6,095,651, or the like.

Based on the measurements of the eye, a corneal ablation pattern may be calculated 44 by processor 22 (or by a separate processor) for ablating the eye with system 10 so as to correct the optical errors of the eye. Such calculations will often be based on both the measured optical properties of the eye and on the characteristics of the corneal tissue targeted for ablation (such as the ablation rate, the refractive index, the propensity of the tissue to form "central islands" or decreased central ablation depths within a uniform energy beam, and the like). The results of the calculation will often comprise an ablation pattern in the form of an ablation table listing ablation locations, numbers of pulses, ablation sizes, and or ablation shapes to effect the desired refractive correction. An exemplary method for generating ablation patterns is described in co-pending patent application No. 60/189,633, the full disclosure of which is incorporated herein by reference. Where the refractive error is to be corrected by alternative treatment modalities, alternative treatment plans may be prepared, such as corneal ring implant sizes, or the like.

Rather than directly proceeding to the ablation, another ablation pattern may also be calculated 46 for ablation of a verification lens. The lens verification lens may be calculated based on the measured optical properties of the eye, together with the characteristics of a lens material including the refractive index of the lens material, the ablation rate of the lens material, any ablation shape-effects of the lens material, and/or the like. The verification lens may then be aligned with the ablation system and ablated 48, optionally using a system similar to that shown in WO 98/23735, which is also incorporated herein by reference. The ablation material will often comprise a polymer such as PMMA, a proprietary material such as the calibration material commercially available from VISX, Incorporated, or the like. The ablation material may optionally be in the form of a credit-card like card, with at least a portion of the ablation material adapted to accept written information.

An aperture is selected with a size corresponding to a size of the pupil, and the aperture and verification lens are mounted to a trial frame 50. Visual acuity is measured 52 with patient wearing the trial frame, allowing the eye to automatically align with the verification lens by moving the head of the patient and the verification lens as the patient scans the eye chart. If the measured visual acuity is equal to or better than some predetermined value, optionally 20/15 or better, the eye is ablated with the planned ablation pattern 54. If not, a second measurement may be taken and the process repeated, and if acuity still remains unacceptable, the ablation may not be performed 56.

Figure 3:
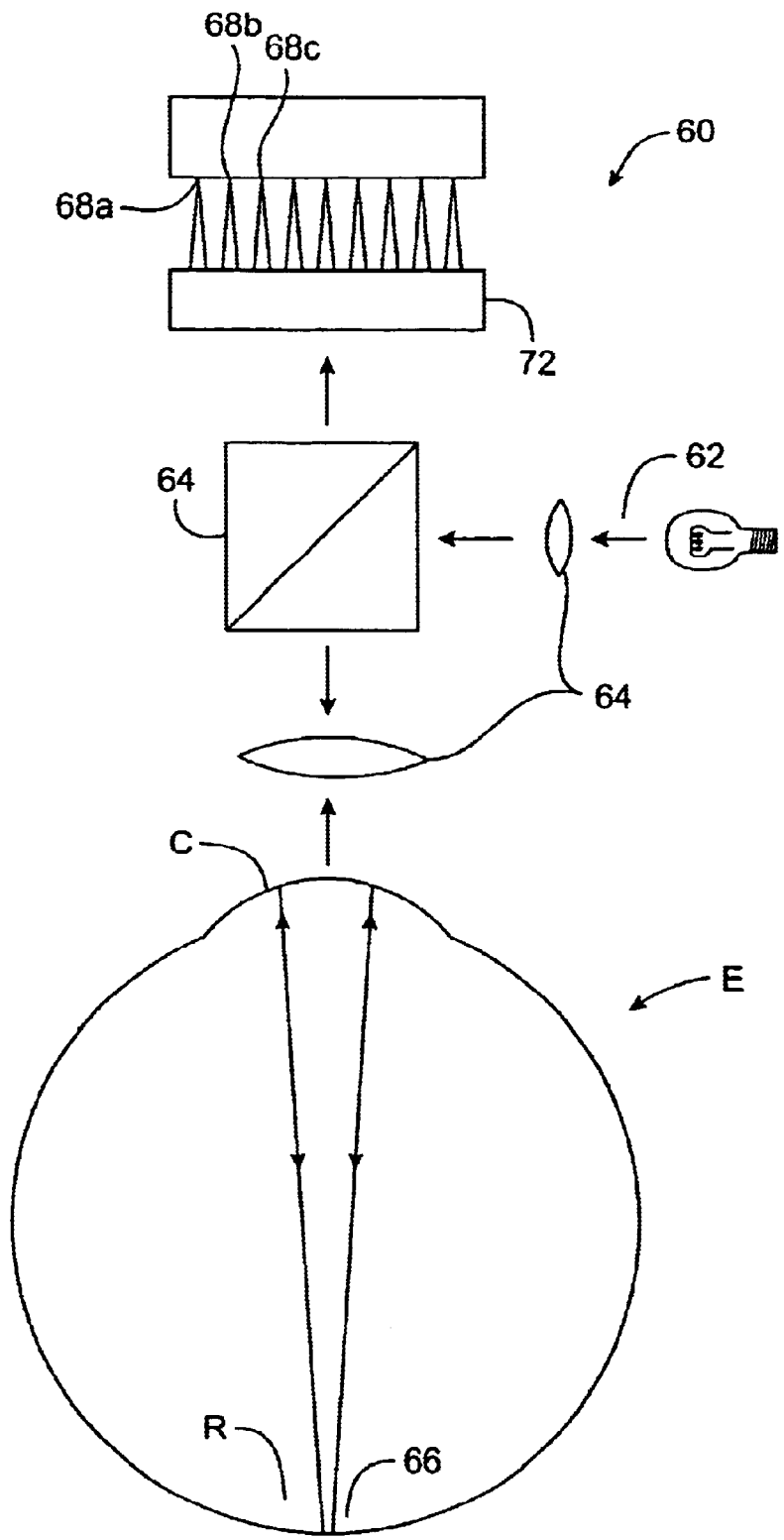
FIG. 3 schematically illustrates wavefront measurements of the eye with a wavefront sensor.

FIG. 3 schematically illustrates wavefront measurements of the eye with a wavefront sensor system 60, as generally described above. Wavefront system 60 projects light 62 using optics 64 toward eye E. Light 62 is transmitted by cornea C of eye E, and forms a retinal image 66 on the retina R of eye E. Wavefront sensor 60 typically forms a series of images 68a, 68b, 68c, . . . (collectively images 68) on a sensor surface 70, often using a microlens array 72 in combination with at least a portion of optics 64. Images 68, 68b, 68c, . . . are each also formed in part by a corresponding portion of cornea C, so that he images 68 can be analyzed to determine local refractive properties and errors across the cornea. These wavefront analysis techniques optionally make use of Zernike polynomials, as is described by references in the field. Alternative analysis methods and wavefront systems are described in U.S. Provisional Application No. 60/259,313, entitled Direct Wavefront-Based Corneal Ablation Treatment Program, the full disclosure of which is incorporated herein by referenced.

FIGS. 4A-C illustrate a verification lens material 80 in which indicia of a lens orientation and position may be provided by silk-screening or the like. The indicia may indicate an upward direction of the verification lens relative to the patient, which may be oriented downward when viewed in the microscope of system 10. The indicia may indicate an identity of the patient 82a, a date of a procedure and/or measurement 82b, a particular eye (left or right) of the patient 82c, a doctor, a system or treatment tracking number, or the like. The indicia will preferably be alignable with a reticule of the ablation system 10 as seen in the microscope to assist in registering or aligning the lens material with the ablation system.

Figure 5:
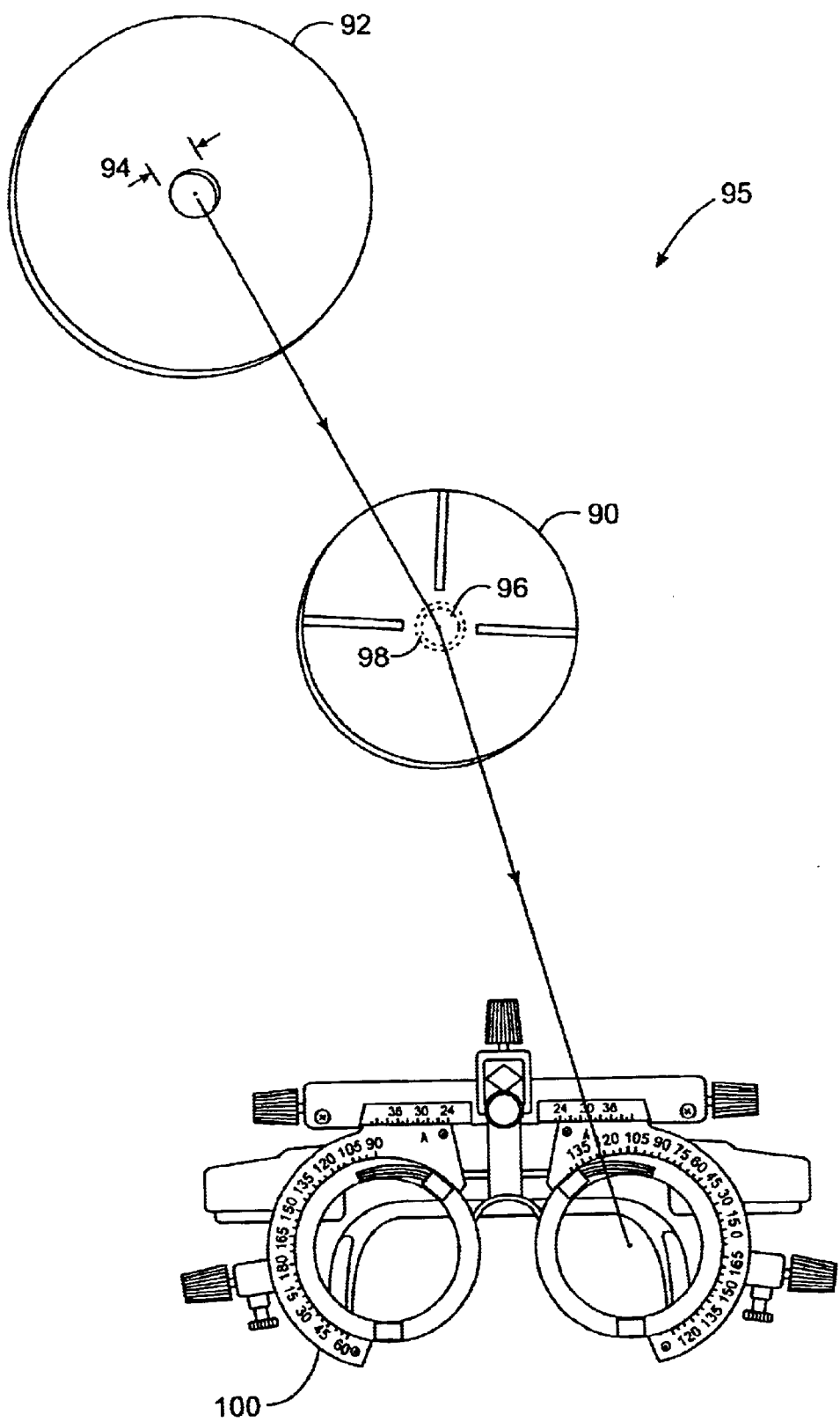
FIG. 5 illustrates an exploded view of an assembly including a verification lens and a selected aperture mounted on a trial frame for testing of corrected visual acuity.

FIG. 5 illustrates an ablated verification lens 90 and an associated aperture 92 included in an assembly 95. The aperture will often be selected from a plurality of apertures to have a size 94 corresponding to a pupil of the patient. The optically used portion of the verification lens will often be encompassed by this aperture, while any transition zone beyond the optically used portion can be excluded when testing of corrected visual acuity with the verification lens. Alternatively, an adjustable aperture iris or the like might be provided. The verification lens 90 and aperture 92 are mounted on a trial frame 100.

Figure 6:
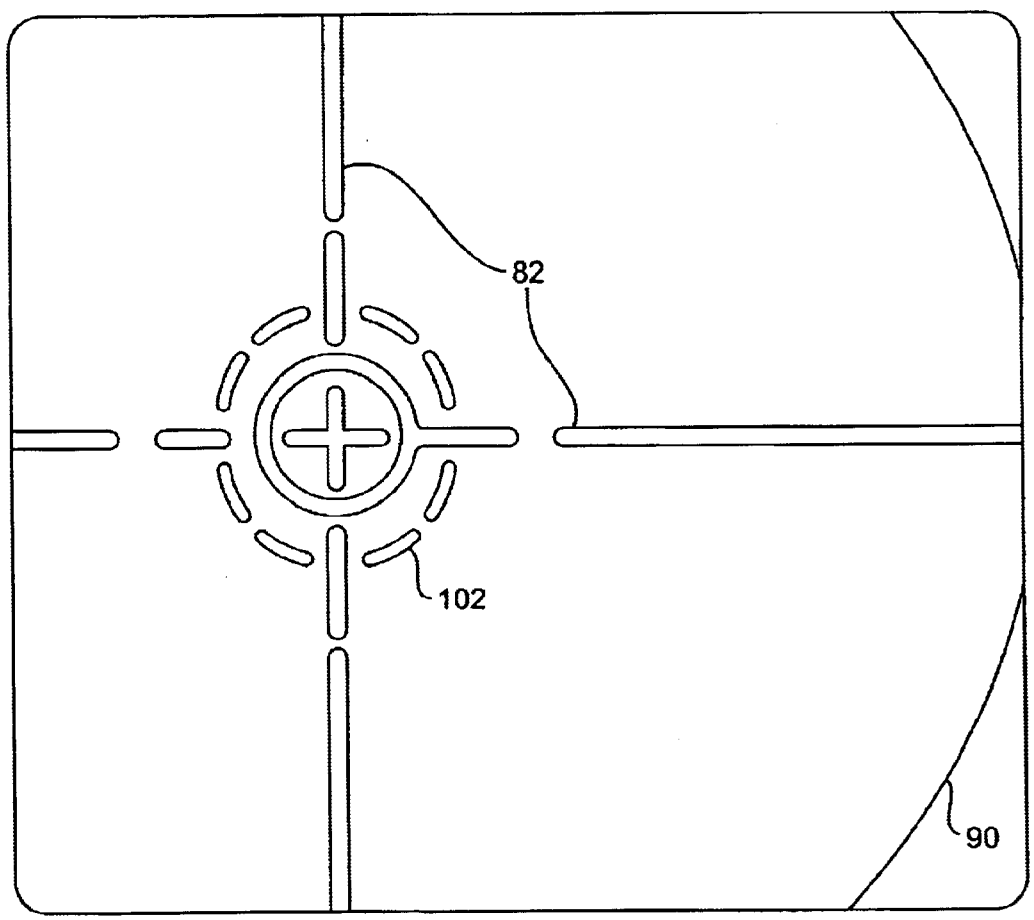
FIG. 6 illustrates alignment of the verification lens material with a reticule of the laser ablation system, as seen through the system microscope.
Figure 7:
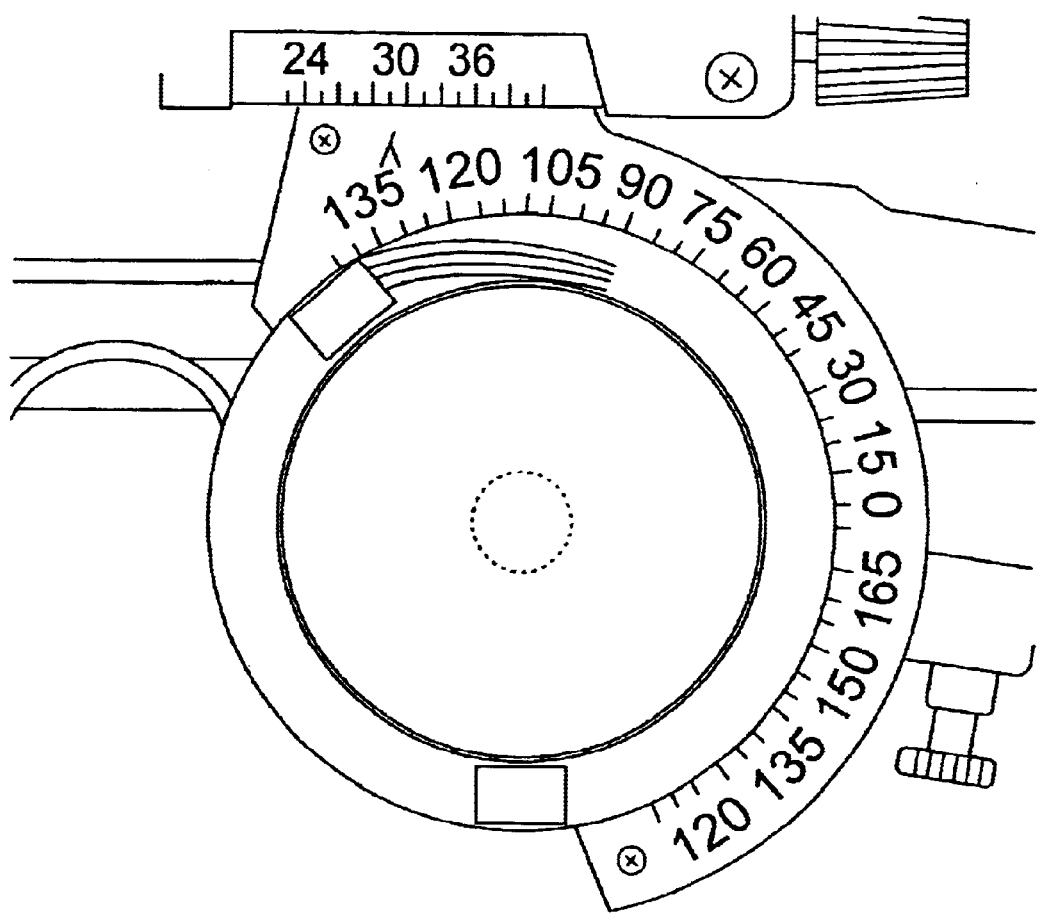
FIG. 7 illustrates a portion of the assembly of FIG. 5, showing alignment of the aperture and the verification lens with a trial frame.

FIG. 6 illustrates alignment of the verification lens material 90 with a reticule 102 of the laser ablation system, as seen through the system microscope 20. The aligned verification lens material may then be ablated as described above regarding FIG. 1, with the verification lens material being supported at the location typically occupied by the cornea of patient P. FIG. 7 illustrates alignment of the aperture and the verification lens as mounted on a trial frame. Trial frames are widely available for mounting of lenses to a head of a patient.

Figure 8:
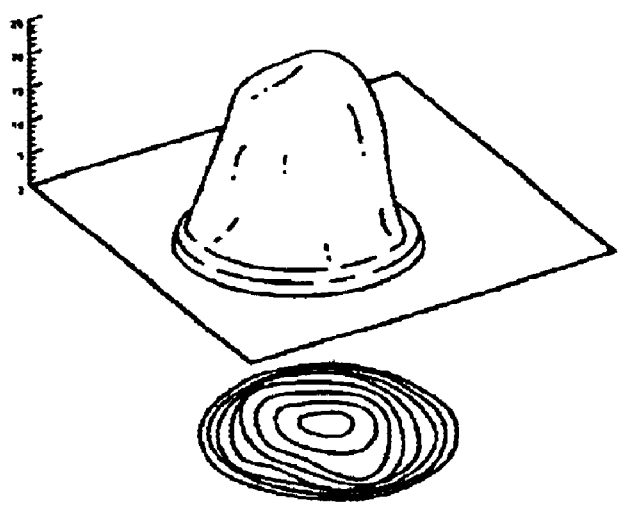
FIG. 8 illustrates a measured wavefront shape for generating an eye ablation pattern.
Figure 9:
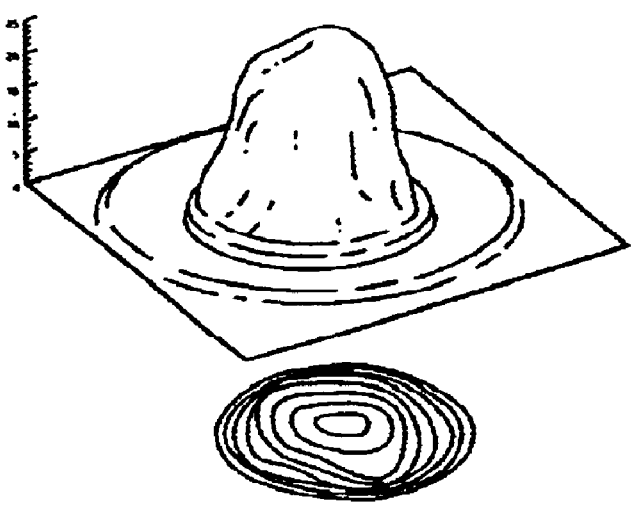
FIG. 9 illustrates a measured ablation of a verification lens based on the measured wavefront shape of FIG. 8.

FIG. 8 illustrates a measured wavefront shape for generating an eye ablation pattern, while FIG. 9 illustrates a measured ablation of a verification lens based on the measured wavefront shape of FIG. 8.

Figure 10:
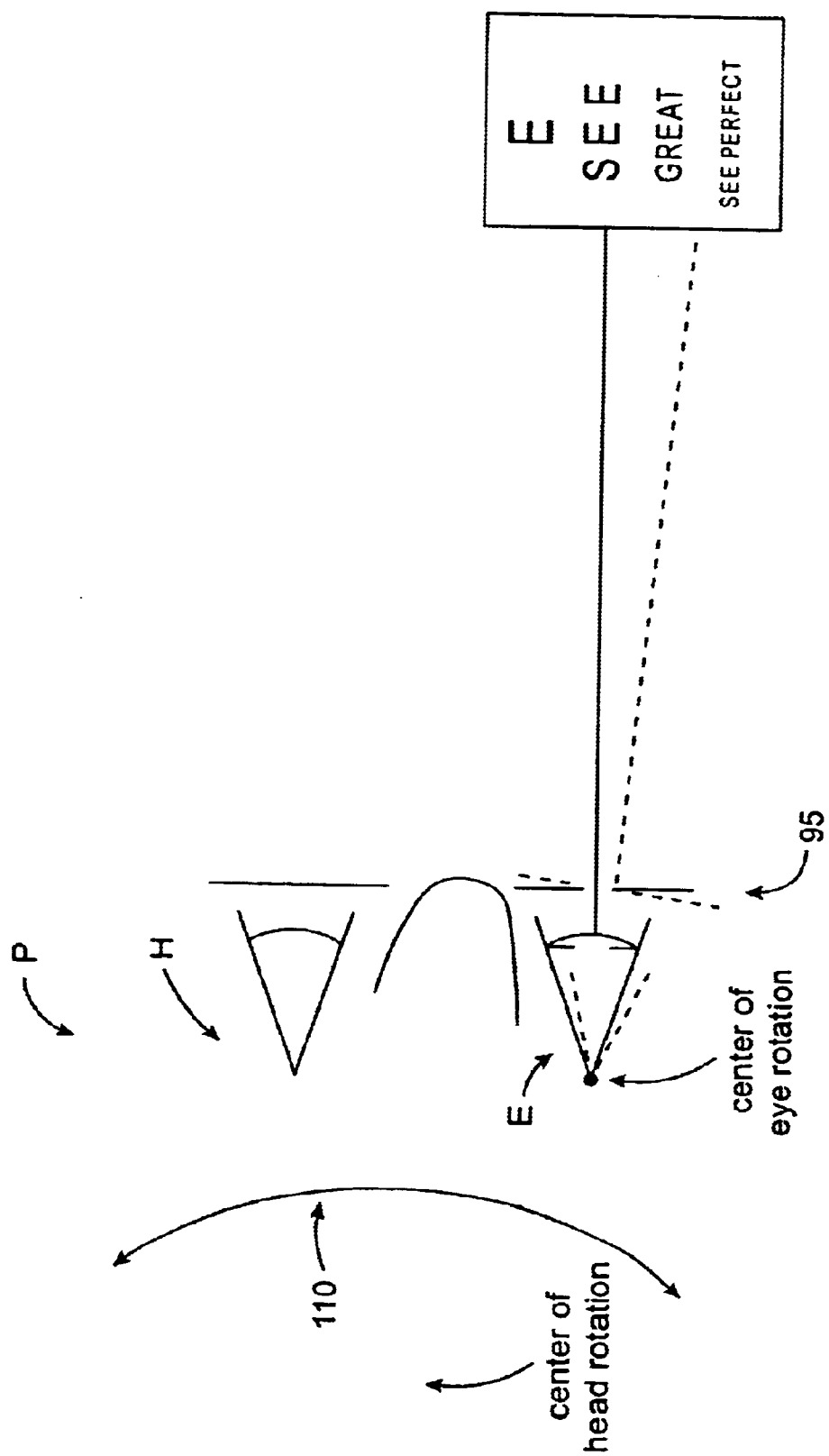
FIG. 10 schematically illustrates autoalignment of a verification lens with an eye by movement of the head relative to an eye chart.

Referring now to FIG. 10, the invention also provides improved methods for aligning a verification lens with the eye while measuring visual acuity. These methods take advantage of autoalignment, which encompasses mounting of the lens 90 to the head with a trial frame to allow the patient to move the head and eye to bring the verification lens into alignment with the eye. The method comprises measuring an actual optical error of an eye of a patient with a wavefront sensor, generating an ablation pattern from the measured optical error, and generating an ablation pattern for a lens material corresponding to the ablation pattern for the eye, as described above FIG. 10 shows a method for selecting an eye of a patient for refractive surgery, in which the verification lens ablation is autoaligned with the eye by rotating 110 the head H of the patient P with the verification lens fixed to the head (by a trial frame or the like). The visual acuity of the eye is measured by reading an eye chart through the autoaligned verification lens, and optionally by maintaining alignment between the eye E and lens 90 using rotation of head H rather than (or in combination with) rotation of eye E as the patient scans the chart.

The invention provides systems and methods for verifying and/or correcting optical errors of an eye. A plan is generated for a corrective procedure of the eye from the measured optical error, and a verification lens is formed based on the measured optical error to verify the procedure plan. Alignment of an aperture (with a size selected to correspond to the size of the pupil) with the eye while measuring optical properties of the eye through the verification lens improves verification accuracy, as does mounting of the verification lens and aperture to the patient with a trial frame.

A variety of refinements, adaptations, and modifications are possible within the scope of the present invention. Hence, the scope of the present invention is not limited to the specifics of the exemplary embodiment, but is instead limited solely by the appended claims.

What is claimed is:

1. A method comprising:
   measuring an actual optical error of an eye;
   generating a plan for a corrective procedure of the eye from the measured optical error; and
   forming a verification lens based on the measured optical error to verify the procedure plan; and
   measuring a visual acuity of the eye as better than 20/20 with the verification lens while exposing an ablated surface of the verification lens.

2. The method of claim 1, further comprising measuring irregular optical error of the eye, wherein the verification lens compensates for the irregular error.

3. The method of claim 2, further comprising measuring a wavefront of light passing through the optical components of the eye with a wavefront sensor to measure a refractive error of the eye.

4. The method of claim 3, wherein the verification lens is generated by ablating a lens material according to an ablation pattern, and further comprising calculating the ablation pattern for the verification lens from the measured optical error of the eye, and from at least one member selected from the group consisting of a refractive index of the lens material, a rate of ablation of the lens material, and a shape of ablation of the lens material.

5. The method of claim 4, further comprising ablating a corneal tissue of the eye according to an ablation pattern, and further comprising calculating the ablation pattern for the corneal tissue from the measured optical error of the eye, and from at least one member selected from the group consisting of a refractive index of the corneal tissue, a rate of ablation of the corneal tissue, and a shape of ablation of the corneal tissue material.

6. A method comprising:
   measuring an actual optical error of an eye of a patient with a wavefront sensor;
   generating an ablation pattern from the measured optical error, and generating an ablation pattern for a lens material corresponding to the ablation pattern for the eye;
   positioning the lens material relative to an ablation system by aligning indicia of the lens material with a reference structure of the ablation system;
   ablating a verification lens in the aligned lens material with the ablation system;
   aligning an aperture with the verification lens;
   mounting the verification lens and the aperture to the patient so that the eye is aligned with the verification lens;
   reading an eye chart with the eye through the verification lens and the aperture while exposing an ablated surface of the verification lens to determine whether a corrected visual acuity of the eye is better than 20/20 so as to verify the ablation pattern of the eye.

7. A system for correcting an optical error of an eye, the system comprising:
   a sensor for measuring the optical error of the eye;
   a processor for generating a verification pattern of laser energy corresponding to a refractive procedure plan of the eye, the procedure plan intended to correct the measured optical error;
   a lens material;
   a laser system for directing laser energy onto the lens material according to the verification pattern so as to form a verification lens from the lens material such that optical properties of the eye, as corrected by the verification lens with an exposed ablated surface, can verify the procedure plan with a visual acuity better than 20/20.

8. A system for correcting an actual optical error of an eye, the system comprising:
   a sensor for measuring the optical error of the eye;
   a processor for generating a pattern of laser energy for ablation of the eye so as to correct the measured optical error, and for generating a verification pattern of laser energy corresponding to the eye ablation pattern;
   a lens material having indicia of alignment;
   a laser system for directing laser energy onto the lens material according to the verification pattern so as to form a verification lens from the lens material, the laser system having a reference structure corresponding with the indicia of alignment so as to ensure registration of the verification pattern on the lens material, the verification lens providing a visual acuity for the eye better than 20/20 while an ablated surface of the verification lens is exposed;
   aperture means for alignment of an aperture with the verification lens, the aperture means having an aperture size selected in response to a size of a pupil of the eye; and
   mounting means for supporting the verification lens and aperture in alignment with the patient while a head of the patient moves to read an eye chart.

9. A method for selecting an eye of a patient for refractive surgery, the method comprising:
- measuring an actual optical error of the eye of the patient with a wavefront sensor;
- generating a first ablation pattern from the measured optical error, and generating a second ablation pattern for a lens material, the second ablation pattern corresponding to the first ablation pattern for the eye;
- ablating a verification lens with the ablation system;
- aligning the second ablation pattern with the eye by rotating the head of the patient with the verification lens fixed to the head; and
- measuring the visual acuity of the eye to be better than 20/20 with the verification lens by reading an eye chart while exposing an ablated surface of the verification lens.

10. The method of claim 9, when the aligning step comprises autoaligning the second ablation pattern with the eye.

11. A system for verifying a specific refractive error of a patient, the system comprising:
- a verification lens having optical properties compensating for the specific refractive error of the patient, the verification lens providing a visual acuity for the eye better than 20/20 while an ablated surface of the verification lens is exposed;
- an aperture aligned with the verification lens; and
- a trial frame supporting the verification lens and aperture.

* * * * *